United States Patent
Bhatt et al.

(10) Patent No.: US 9,734,182 B2
(45) Date of Patent: Aug. 15, 2017

(54) INGREDIENT BASED NUTRITIONAL INFORMATION

(71) Applicant: International Business Machines Corporation, Armonk, NY (US)

(72) Inventors: Dhruv A. Bhatt, Indian Trail, NC (US); Kristin E. McNeil, Charlotte, NC (US); Soomi Mun, Stallings, NC (US); Nitaben A. Patel, Charlotte, NC (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/087,857

(22) Filed: Mar. 31, 2016

(65) Prior Publication Data

US 2017/0031995 A1    Feb. 2, 2017

Related U.S. Application Data

(63) Continuation of application No. 14/811,997, filed on Jul. 29, 2015.

(51) Int. Cl.
G06F 7/00    (2006.01)
G06F 17/30    (2006.01)
(Continued)

(52) U.S. Cl.
CPC .... *G06F 17/30339* (2013.01); *G06F 17/2276* (2013.01); *G06F 17/30345* (2013.01);
(Continued)

(58) Field of Classification Search
CPC .................................................. G06F 17/2276
See application file for complete search history.

(56) References Cited

U.S. PATENT DOCUMENTS

| 7,541,548 B1 | 6/2009 | Sze et al. |
| 2006/0122468 A1 | 6/2006 | Tavor |

(Continued)

FOREIGN PATENT DOCUMENTS

| AU | 2005292744 A1 | 4/2006 |
| EP | 1030245 A2 | 8/2000 |

(Continued)

OTHER PUBLICATIONS

Hamon et al., "Extraction of Ingredient Names from Recipes by Combining Linguistic Annotations and CRF Selection," CEA '13 Proceedings of the 5th International Workshop on Multimedia for Cooking & Eating Activities, Oct. 2013, pp. 63-68, © 2013 ACM, New York, NY. DOI: 10.1145/2506023.2506035.

(Continued)

*Primary Examiner* — Ajith Jacob
(74) *Attorney, Agent, or Firm* — Nathan M. Rau

(57) ABSTRACT

Nutritional information of a recipe is gathered to determine a nutritional value table of a food recipe. A computing device may extract and analyze unstructured text of a food recipe to obtain a plurality of ingredients and a quantity of the plurality of ingredients. The computing device may access dietary preferences of a user. The nutritional information of the food recipe may be calculated using the nutritional value of each of the ingredients and complied into a nutritional value table. The recipe may be determined if the recipe corresponds with the dietary preferences of the user. If a recipe does not correspond with the dietary preferences, then an ingredient causes the recipe to not correspond with the dietary preferences is removed from the recipe creating an altered recipe. The nutritional value table of the altered recipe is displayed to the user.

1 Claim, 9 Drawing Sheets

(51) Int. Cl.
*G09B 19/00* (2006.01)
*G06F 17/22* (2006.01)
*G06Q 10/10* (2012.01)

(52) U.S. Cl.
CPC .. *G06F 17/30368* (2013.01); *G06F 17/30507* (2013.01); *G06F 17/30528* (2013.01); *G06Q 10/10* (2013.01); *G09B 19/0092* (2013.01)

(56) References Cited

U.S. PATENT DOCUMENTS

| | | | |
|---|---|---|---|
| 2009/0275002 | A1 | 11/2009 | Hoggle |
| 2012/0096087 | A1 | 4/2012 | Curcelli |
| 2014/0200879 | A1 | 7/2014 | Sakhai et al. |
| 2014/0324899 | A1 | 10/2014 | Sherman et al. |
| 2015/0046493 | A1 | 2/2015 | Akselrod et al. |

FOREIGN PATENT DOCUMENTS

| | | | |
|---|---|---|---|
| WO | 98/45766 | A1 | 10/1998 |
| WO | 2006038820 | A2 | 4/2006 |

OTHER PUBLICATIONS

Meijers, N., "Edamam Helps People Eat Better Through Nutrition Data," Food + Tech Connect, Jan. 21, 2015, (accessed Mar. 9, 2015), pp. 1-3. http://www.foodtechconnect.com/2015/01/21/edamamorganizeworldsfoodknowledge/.

Mell et al., "The NIST Definition of Cloud Computing: Recommendations of the National Institute of Standards and Technology," NIST Special Publication 800-145, Sep. 2011, 7 total pages, National Institute of Standards and Technology, U.S. Department of Commerce, Gaithersburg, MD.

Van Pinxteren et al., "Deriving a Recipe Similarity Measure for Recommending Healthful Meals," IUI '11 Proceedings of the 16th International Conference on Intelligent User Interfaces, Feb. 2011, pp. 105-114, © 2011 ACM, New York, NY. DOI: 10.1145/1943403.1943422.

Unknown, "USDA National Nutrient Database for Standard Reference", Release 27, United States Department of Agriculture, pp. 1-2, (last modified Sep. 2, 2014). http://www.ars.usda.gov/Services/docs.htm?docid=8964.

Bhatt et al., "Ingredient Based Nutritional Information," U.S. Appl. No. 14/811,997, filed Jul. 29, 2015.

List of IBM Patents or Patent Applications Treated as Related, signed Jul. 21, 2016, 2 pgs.

INGREDIENT BASED NUTRITIONAL INFORMATION

BACKGROUND

Aspects of the present disclosure relate to data processing information retrieval, and more particular aspects relate to extracting text using data mining and text analytics to generate nutritional information.

Text analytics may be used to generate a desired structured output from unstructured text. By using patterns and trends within text, high-quality information may be gathered and compiled into a desired output. Text analytics may be paired with a query to display relevant information based on the information gathered. Text analytics may be used to generate a desired structured output from unstructured text. For example, text analytics may be implemented into a question answer system to gather and display relevant information associated with the answer. The answer may then be gathered by an input query.

SUMMARY

According to embodiments of the present disclosure, a computer implemented method is proposed to perform text analysis. The text analysis may be used to transform text of a recipe to data. The data may be used in conjunction with a database to provide nutritional information to a user.

One embodiment provides a method for determining nutritional information of a recipe by gathering the ingredients from unstructured text of a recipe. The ingredients are gathered to determine a nutritional value table of a food recipe. A computing device may extract and analyze unstructured text of a food recipe to obtain a plurality of ingredients and a quantity of the plurality of ingredients. The computing device may access dietary preferences of a user. The nutritional information of the food recipe may be calculated using the nutritional value of each of the ingredients. The nutritional information of the plurality of ingredients may be compiled into a nutritional value table. The recipe may be determined if the recipe corresponds with the dietary preference. The recipe may include a non-corresponding ingredient that is does not correspond with the dietary preferences of the user. The non-corresponding ingredient that is outside the dietary preferences of the user may be located. The recipe is altered by removing the non-corresponding ingredient. The nutritional value table of the altered recipe is displayed to the user.

Another embodiment is directed toward a system for determining nutritional information of a recipe by gathering the ingredients from unstructured text of a recipe. The system includes a memory, a processor device communicatively coupled to the memory, and an application stored on the memory communicatively coupled to the processor device. The application is configured to extract and analyze unstructured text of a food recipe to obtain a plurality of ingredients and a quantity of the plurality of ingredients. The application is configured to access dietary preferences of a user. The application is configured to calculate the nutritional information of the food recipe using the nutritional value of each of the ingredients. The application is configured to compile the nutritional information of the plurality of ingredients into a nutritional value table. The application is configured to determine if the recipe corresponds with the dietary preference. The application is configured to determine that the recipe includes an ingredient that is does not correspond with the dietary preferences of the user. The application is configured to locate the non-corresponding ingredient. The application is configured to alter the recipe by removing the non-corresponding ingredient. The application is configured to display the nutritional value table of the altered recipe to the user.

Yet another embodiment is directed toward a computer program product for determining nutritional information of a recipe by gathering the ingredients from unstructured text of a recipe. The computer program product is configured to extract and analyze unstructured text of a food recipe to obtain a plurality of ingredients and a quantity of the plurality of ingredients. The computer program product is configured to access dietary preferences of a user. The computer program product is configured to calculate the nutritional information of the food recipe using the nutritional value of each of the ingredients. The computer program product is configured to compile the nutritional information of the plurality of ingredients into a nutritional value table. The computer program product is configured to determine if the recipe corresponds with the dietary preference. The computer program product is configured to determine that the recipe includes an ingredient that is does not correspond with the dietary preferences of the user. The computer program product is configured to locate the non-corresponding ingredient that is the dietary preferences of the user. The computer program product is configured to alter the recipe by removing the non-corresponding ingredient. The computer program product is configured to display the nutritional value table of the altered recipe to the user.

The above summary is not intended to describe each illustrated embodiment or every implementation of the present disclosure.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

Figure 1:
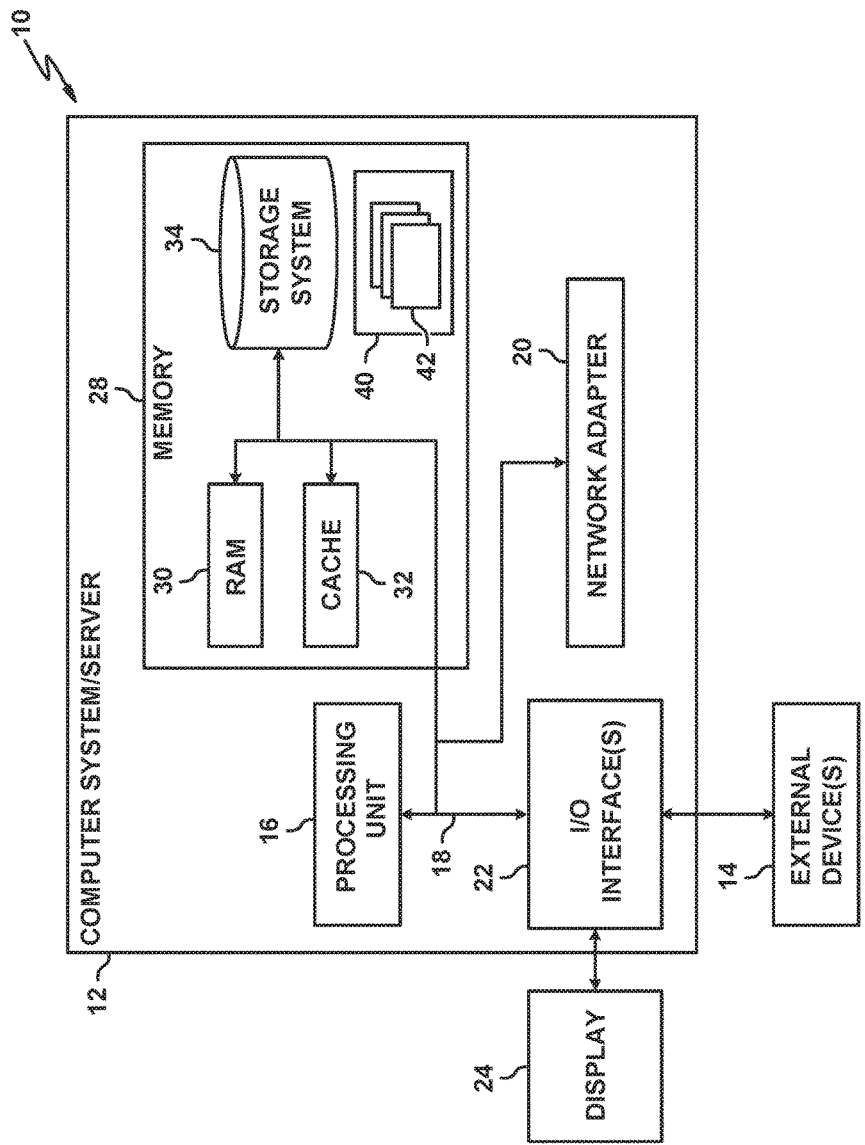
FIG. 1 depicts a cloud computing node, according to embodiments of the present disclosure.

While the embodiments described herein are amenable to various modifications and alternative forms, specifics thereof have been shown by way of example in the drawings and will be described in detail. It should be understood, however, that the particular embodiments described are not to be taken in a limiting sense. On the contrary, the intention is to cover all modifications, equivalents, and alternatives falling within the spirit and scope of the invention.

DETAILED DESCRIPTION

Aspects of the present disclosure provide a method, a system, and a computer program product to extract nutritional information for a food recipe based on ingredients. The food recipe may include a plurality of ingredients. The method, the system, and the computer program product may provide a nutritional value table including compiling the nutritional information of the plurality of ingredients of the food recipe. Based on the nutritional value table of the recipe, an alert system may alter the recipe to suit a dietary preference of the user. If the recipe does not follow the dietary preference of the user, then the recipe may be altered or rejected based on the non-corresponding ingredient.

Depending on the weight, height, gender, and activity level of a person, their diet may be different. Typically, human diets may be fairly consistent between humans with the similar weighs, heights, and gender. However, complications in diet may occur when a human develops a disease (e.g. illness) that requires a specific diet. Additionally, some individuals may also have specific self-imposed diets. Self-imposed diets may include reduction in an intake of specific nutrient(s), increase in an intake of specific nutrient(s), or a removal of a specific nutrient/ingredient composition from their diet. For example, if an individual wishes to lose weight, then a self-imposed diet may include reducing specific nutrients such as sugar and fats. In another example, if an individual exercises regularly, they may require an increase in specific nutrients into their diet such as fats and carbohydrates. In another example, if an individual maintains a restrictive diet of vegetarianism, they may remove foods manufactured with or including animals from their daily intake. The individual with the vegetarian diet may see a reduction in protein and fats from not consuming meats, which the individual may substitute with other foods containing protein and fats.

When reading a nutritional information table on a packaged meal an individual may decide if the meal is appropriate for their daily intake and regimen their day intake for the rest of the day based on choices made earlier. To inform the individual of nutritional information that may be found in a nutritional value table, ingredients and the quantities of the ingredients of a meal may be gathered to determine the nutritional value of the meal. A prepackage meal may gather the nutritional information of the meal and display the nutritional information on a nutritional value table. Although reading the nutritional value table may give the individual information about the meal, a recipe may not provide the nutritional value table for the meal. To provide the individual with the nutritional value of the meal from a recipe, information of the recipe may be gathered and analyzed using text analytics.

Determining nutritional information when searching through food recipes (recipes) may prove difficult to determine the health advantages and disadvantages when meal planning. Determining nutritional information when searching through food recipes may prove to be difficult when trying to determine the health consequences of a particular meal. For instance, the nutritional advantages of particular ingredients within the food recipe may not always be well known without searching for additional information. To understand what nutritional value (e.g. through the nutritional information) the food recipe contains an ingredient list may be analyzed to determine a nutritional value table. The nutritional value table may contain the nutrition information that the food offers. The nutritional information of the recipe may include nutritional indicators of the nutritional value table. The nutrition value table may include nutrition indicators such as proximates, minerals, vitamins, lipids, and other constituents of the ingredient. The nutrition indicators may include the chemical makeup of the ingredients that may be grouped together. Nutrition indicators that are grouped together may include total lipids or sugars. For example, trans-fats, saturated fats, monosaturated fats, and cholesterol may all be listed individually, but may also be listed under the total lipids category. The types of nutrition/nutritional indicators will be described further herein.

A nutritional value table contains a compilation of the nutritional information (nutritional properties) of a collection of ingredients. The collection of ingredients may include a plurality of ingredients that when combined create a food recipe. The nutritional value table may include the nutritional information of each of the plurality of ingredients, and when combined the nutritional information of each of the ingredients may become a part of the nutritional value table. For example, a food recipe of fried chicken may contain chicken, eggs, flour, breadcrumbs, salt, pepper, paprika, and vegetable oil. The nutritional value table may combine the calories (kcal) of each of the ingredients in the food recipe to give the calories of the whole food recipe in the nutritional value table. The combed calories before cooking may be 880 kcal.

Determining nutritional information when searching through recipes may prove to be difficult when trying to determine the health consequences of a particular meal. Many foods contain nutritional advantages that are not always well known without searching databases specifically for that ingredient. Other foods contain nutritional disadvantages that may be known but not easily recognized.

In some instances, an individual may have to follow a health related diet. Health related diets might include diets that restrict the individual from consuming certain ingredients/nutrients based on a health condition or intolerance. In some circumstances, diets may be prescribed by a doctor to increase recovery speed or prevent issues with diseases. Special diets or dietary preferences may be used by the individual to eat healthier or overcome a health condition. The dietary preference may restrict the user to a diet that may limit the intake of a certain nutritional indicator or ingredient. For example, a dietary preference may include the user restricting their daily intake of calories by consuming healthier meal options. A health condition may include an illness where a diet may be suggested. A diet, which requires the individual to consume a certain ingredient/nutrient, may be a restrictive diet. For example, people with high blood pressure may follow a restrictive diet that is low in sodium by reducing foods in their diet that are high in salt. The individual with high blood pressure may limit their diet to reduce foods that are high in salt to reduce their blood pressure. In another example, people with kidney disease may follow a restrictive diet by reducing their intake of foods high in potassium. In another example, people with diabetes may follow a restrictive diet of foods high in sugars, like candy or sugary beverages. A diet, which required the individual to consume more of an ingredient/nutrient, may be an inclusive diet. In an example, people with deficiencies in minerals like the mineral iron, may increase their intake of foods high in iron.

Proximates consist of the basic digestible nutrients within a human diet. For example, proximates may include ash, moisture, proteins, total lipid (fat), carbohydrates (carbs), and energy. Energy may be referred to as calories measured in kilocalories (kcal). Carbohydrates or carbs may consist of sugars and dietary fibers that may be combined to determine the total carbohydrates. Sugars and dietary fibers may also be listed separately along with the carbohydrates. Ash may consist of the dietary minerals and vitamins both of which will be described further herein.

Minerals may include the naturally occurring elements found in foods. Minerals may be subdivided into two groups. Each mineral may contain a specific function within the human diet. The first group is macrominerals may include minerals that have a higher intake requirement. Examples of macrominerals may include sodium, chloride, potassium, calcium, phosphorus, magnesium, and sulfur. The second group is microminerals, have a lower intake requirement. The microminerals may also be referred to as trace minerals. Examples of microminerals may include iron, zinc, iodine, selenium, copper, manganese, fluoride, chromium, and molybdenum.

Vitamins may include organic compounds that are essential for growth and nutrition. In an individual, the diet vitamins are required in small quantities because they cannot be synthesized by the body. Many vitamins may be included in the human daily intake for promoting various functions within the body. Vitamins may include vitamin A-D, vitamin D2, vitamin D3, vitamin K, thiamin, riboflavin, niacin, and folate.

Lipids consist of the daily intake of fats in the human diet. Lipids may include saturated fatty acids, monounsaturated fatty acids, polyunsaturated fatty acids, trans fatty acids, and cholesterol. Lipids may be summed up into the total fat listed within the total lipid category in the proximates. In embodiments, the lipids may be separated in to their specific fatty acid category to distinguish the levels of unsaturated fats, saturated fats, and trans fats.

Other listed nutrients that may be included on the nutritional value table. Nutrients that are listed under the other category may include but is not limited to caffeine, ginseng, maltodextrin, and taurine. The other ingredients may not be required by the Federal Drug Administration (FDA) to be listed on the nutritional value table, but may be included.

Nutrient data of ingredients are compiled by the United States Department of Agriculture (USDA). The USDA compiles the nutrient information within a nutrient databank system (NDBS) of the ingredients. Each ingredient is assigned a nutrient databank number (e.g. NDB No.) and is stored within the NDBS. The NDBS may be downloaded and stored within a dictionary to access the nutritional information of an ingredient within a recipe. The dictionary may store current nutritional information as well as be updated when the USDA updates the NDBS.

The dictionary (i.e. repository) may be stored online and accessed through a device with an internet connection. The Dictionary may be stored on a memory of a device and accessed through an application. The application may run on a computing device such as a computer. The dictionary may communicate with a text analyzer, which gathers information from a recipe described further herein.

A text analyzer may be used to gather information from a recipe using text analytics to gather text within the recipe. The text analyzer may use tools, such as unstructured information management architecture (UIMA) or natural language processing (NLP) to gather text. UIMA may be paired with NLP to gather and analyze the information on a recipe. NLP may gather the ingredients and the amounts of the ingredients through annotations within the text. The information may then be converted into a single source of information (i.e. nutritional value table). UIMA may be an architecture that may be used to gather unstructured data from a device or recipe and display relevant information based on the data. Unstructured information may include text, audio, video, or images. UIMA may gather the information that is relevant to determining the nutritional value of the recipe and output the information to the dictionary, which transforms the information. UIMA may contain repositories that contain rules to extract specific phrases or ingredients from the recipe. The repositories maybe updated and maintained to gather ingredients within the recipe. The rules may also include instructions on how to gather the serving size of the recipe, and the quantities of the ingredients. NLP may gather information based on natural language, where the computer derives information based on natural human language. NLP may use UIMA to gather the information and may follow an algorithm to transform the data based on the needs of the text analyzer.

In various embodiments, UIMA may gather the source instructions within a website and use the code to determine the constituents herein used interchangeably with the term ingredients. The constituents may be gathered through annotations, which mark the constituents of the recipe. The annotations may select specific constituents from an unstructured text and gather the text into an ingredient list. The code may include hypertext markup language (HTML) or extensible markup language (XML) as annotations to gather the constituents of the recipe. The HTML or XML of various websites may include a dictionary, or a look up relating to specific items that the UIMA may use to gather the constituents of the recipe. For example, a code in HTML may be given to every ingredient for an online recipe. The UIMA may determine the location of the constituent within the code, determine what the constituent is using the HTML, and gather the relevant information that relates to the constituent. Relevant information may include the amount of the constituent in relation to the constituent, and the unit of measurement of the amount of the constituent in relation to the constituent.

The text analytics may be used to determine the ingredients for the meal and the quantities of the ingredients. The quantities of the ingredients may include the amount of an ingredient as well as the unit of measurement. For example, the ingredient may be nonfat milk, and the quantity may be two cups. The quantity may include the amount as two, and the unit of measurement will be a cup. The unit of measurements may be converted to a single measurement like grams (g) where two cups of nonfat milk would weigh approximately 490 g. Each ingredient including the quantity of the ingredient may be gathered and compared to a database, which may contain the nutritional information of each ingredient. The nutritional information of each of the ingredients may be summated to create a total of nutritional information, which may be displayed on a nutritional value chart. The nutritional value chart may be displayed through a graphical user interface (GUI) to the individual.

In various embodiments, the recipe may also be analyzed to compare dietary restrictions of the individual to the ingredients and nutritional information of the recipe. For example, the individual may have a diet low in sodium. If the individual has a restriction on their sodium intake of 2 g per day, then the recipe may be rejected if the sodium content is high. The recipe may contain 1 g of sodium, which will limit the rest of the meals of the day to be under 1 g of sodium. If the individual determines the sodium of the meal may be too high to eat that day, the individual may choose another meal to eat that day, or remove an ingredient from the recipe.

In various embodiments, a compiler may select ingredients within a recipe. The selecting of the ingredients may include ingredients that may be omitted or substituted based on dietary preferences of an individual. The selecting may include highlighting the ingredient(s) that conflict with the dietary preferences of the individual. For example, if the individual is on a low sodium dietary preference, then ingredients containing high levels of sodium may be selected. If a recipe includes adding salt, the compiler may highlight the salt addition and inform the individual about the added salt. If the recipe calls for a sauce high in sodium (i.e. soy sauce), the compiler may highlight the soy sauce and inform the individual about the sodium levels in the sauce.

In various embodiments, a compiler may inform an individual about how well the recipe follows the dietary preferences of the individual. The recipe may be rated based on how well the recipe follows the dietary preferences of the individual. For example, the recipe may be rated on a scale of 1-10 on how well the recipe follows the dietary preferences of the individual. If the dietary preferences of the individual includes a low calorie diet, then the recipe may be rated from 1-10 based on the caloric content measured in kilocalories (kcal). The rating scale may include 1 being a bad recipe to make and consume a single serving, and a 10 being a good recipe to make and consume a single serving. The low calorie diet may include an 1800 kcal diet and if the recipe includes 450 kcal per serving, the recipe may receive a higher rating of around 6-8. If a recipe includes 900 kcal per serving, the recipe may receive a lower rating of 3-5.

In various embodiments, the recipe may be include splitting the nutritional value table of the recipe into serving sizes. The serving size may be determined by text analytics of the unstructured text of the recipe. If the recipe lists a number of servings, then the nutritional value table may be split into serving sizes. For example, if the number of servings is three, then the nutritional value table, which may include a nutritional value for the whole recipe, may be divided by three. After dividing the nutritional value the nutritional value table may be displayed as a serving size.

Multiple factors may be taken into account by the compiler when determining if the recipe follows the dietary preferences of an individual. For example, calories, total fat, and sugars may be monitored for and the recipe may be rated based on the combination of the three proximates. If the calories and sugar content is low but the total fat content is high, then the recipe may still be given a low rating. For example, the calories for a small meal may be 100 kcal, the sugar content may be 2 g, but the total fat content may be 50 g and the compiler may give the recipe a low rating because the meal gives insufficient calories to total fat content to be consumed.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

While the present disclosure is not necessarily limited to such applications, various aspects of the disclosure can be appreciated through a discussion of various examples using this context.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable the computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 2:
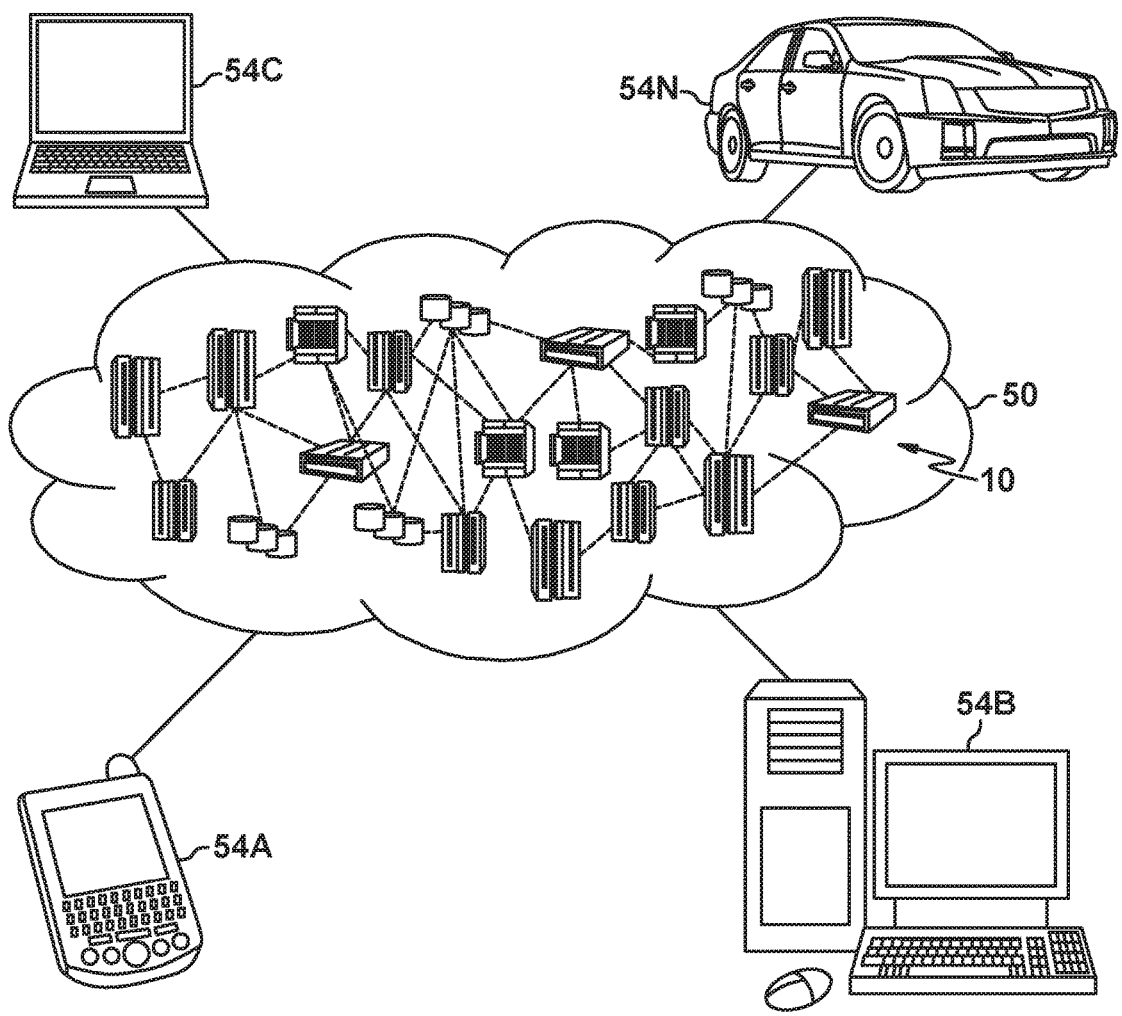
FIG. 2 depicts a cloud computing environment, according to embodiments of the present disclosure.

Referring now to FIG. 2, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
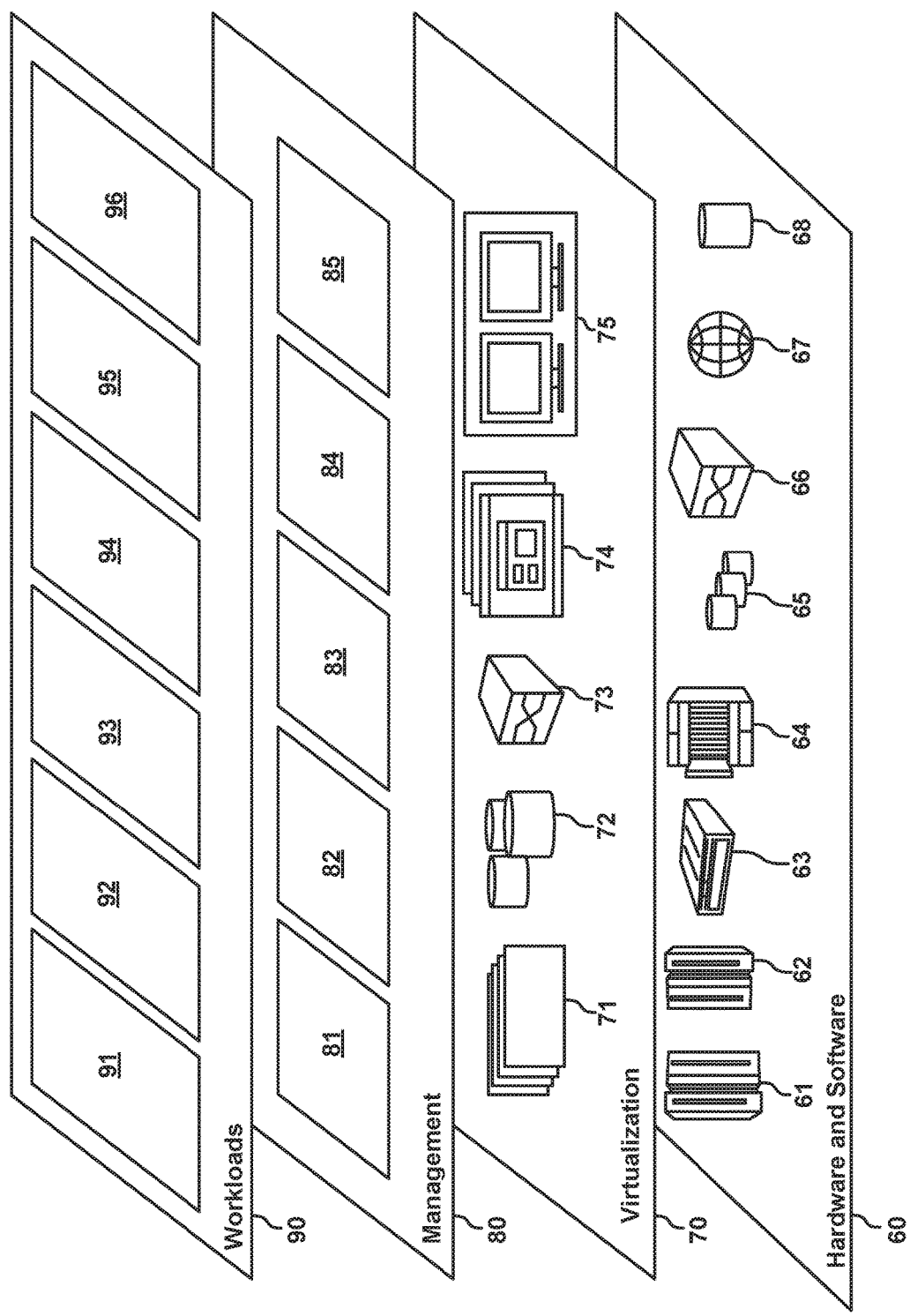
FIG. 3 depicts abstraction model layers, according to embodiments of the present disclosure.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and mobile desktop 96. Data analytics processing 94 may include UIMA to monitor and process data within the cloud computing environment. The cloud computing environment may store applications that utilize NLP and UIMA to gather annotations or data from an unstructured text recipe which may be converted into a nutritional information table.

Figure 4:
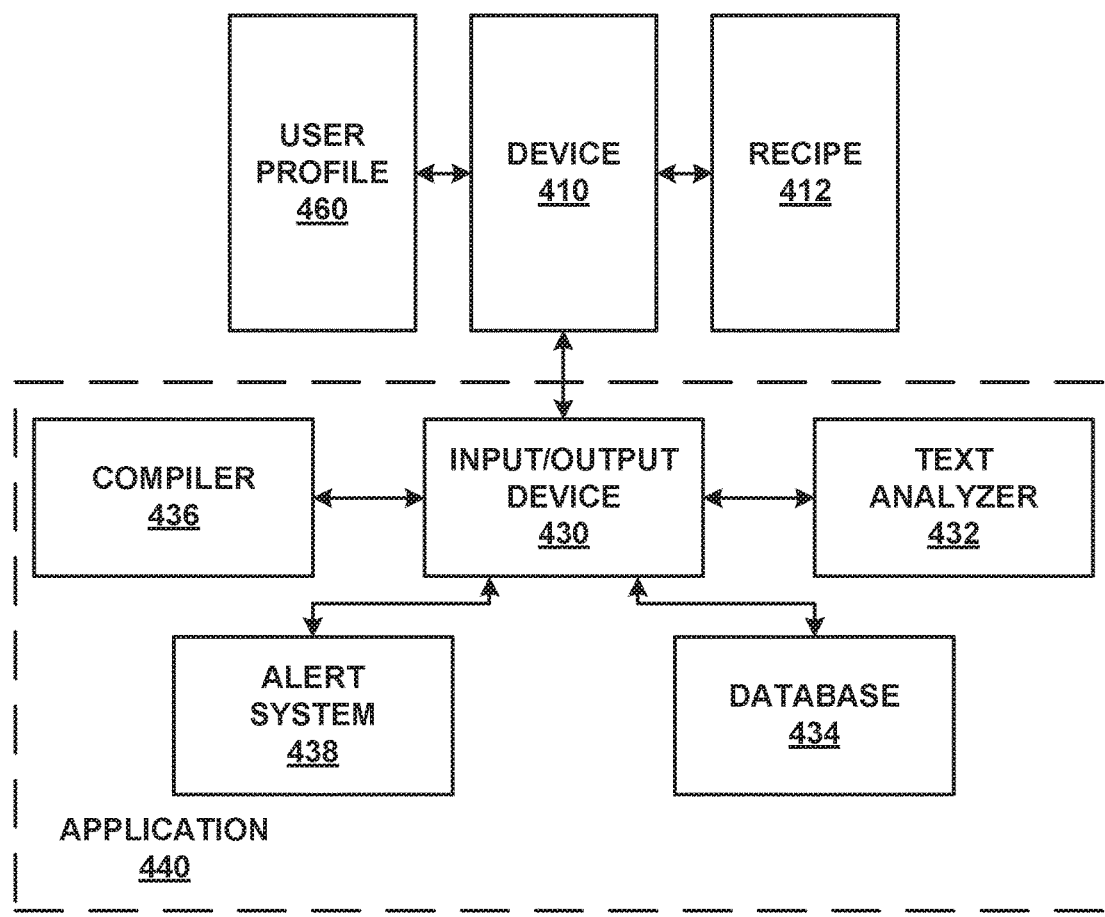
FIG. 4 depicts a diagram of an input/output device accessing the recipe via a user device, according to embodiments of the present disclosure.

FIG. 4 depicts a device gathering the nutritional information of a recipe though an application, according to embodiments. The application 440 may be stored on the device 410 within a memory of the device. The device 410 for example may be a computing device, or a mobile device that the user may operate upon to access a recipe. The application 440 may house an input/output device 430. The input/output device 430 may be in communication with or be an interconnect between a text analyzer 432, a database 434, a compiler 436, and an alert system 438. The input/output device 430 may receive the recipe 412 from the device 410. The input/output 430 device may gather the unstructured text using a text analyzer 432, and send the gathered text back to the input/output device 430 which process the recipe 412, and output the nutritional information back to the device 410. The text analyzer 432 may gather the ingredients and respective quantities from the recipe 412. The text analyzer 432 may utilize UIMA to gather the unstructured text of the recipe. The text analyzer 432 may use NLP to gather the unstructured text of the recipe. The unstructured text may then be utilized by the database 434, which may house a dictionary for determining the nutritional information for each ingredient within the recipe 412 based on the quantities of the ingredients. The database may store the nutritional information of ingredients on a dictionary. The compiler 436, may receive the nutritional information of each of the ingredients within recipe 412 based on the quantities of the ingredients and compile the nutritional information into a nutritional value table. The alert system 438, may alert the user that the recipe 412 does not follow a dietary preferences of the user profile 460.

The device 410 may include a user profile 460. The user profile 460 may include dietary preferences of a user. The dietary preferences of the user may include a diet or health restrictions that the user follows. The user profile 460 may be entered by the user to inform the application 440 on dietary preferences of the user. For example, the user may input a dietary preferences of a low sugar diet. If the recipe 412 does not follow a low sugar diet, then the application 440 may alert the user that the recipe 412 does not follow the dietary preferences of the user.

In various embodiments, the recipe may be gathered through the internet. The input/output device 430 may connect to the internet and access the recipe 412 through the internet. The input/output device 430 may gather the unstructured text from the recipe the same as though the device 410, but through the internet. For example, the input/output device 430 may connect to the internet, and the application may convert the text of the recipe 412 to a nutritional information table. The nutritional value table may then be displayed to the user on the device 410.

Figure 5:
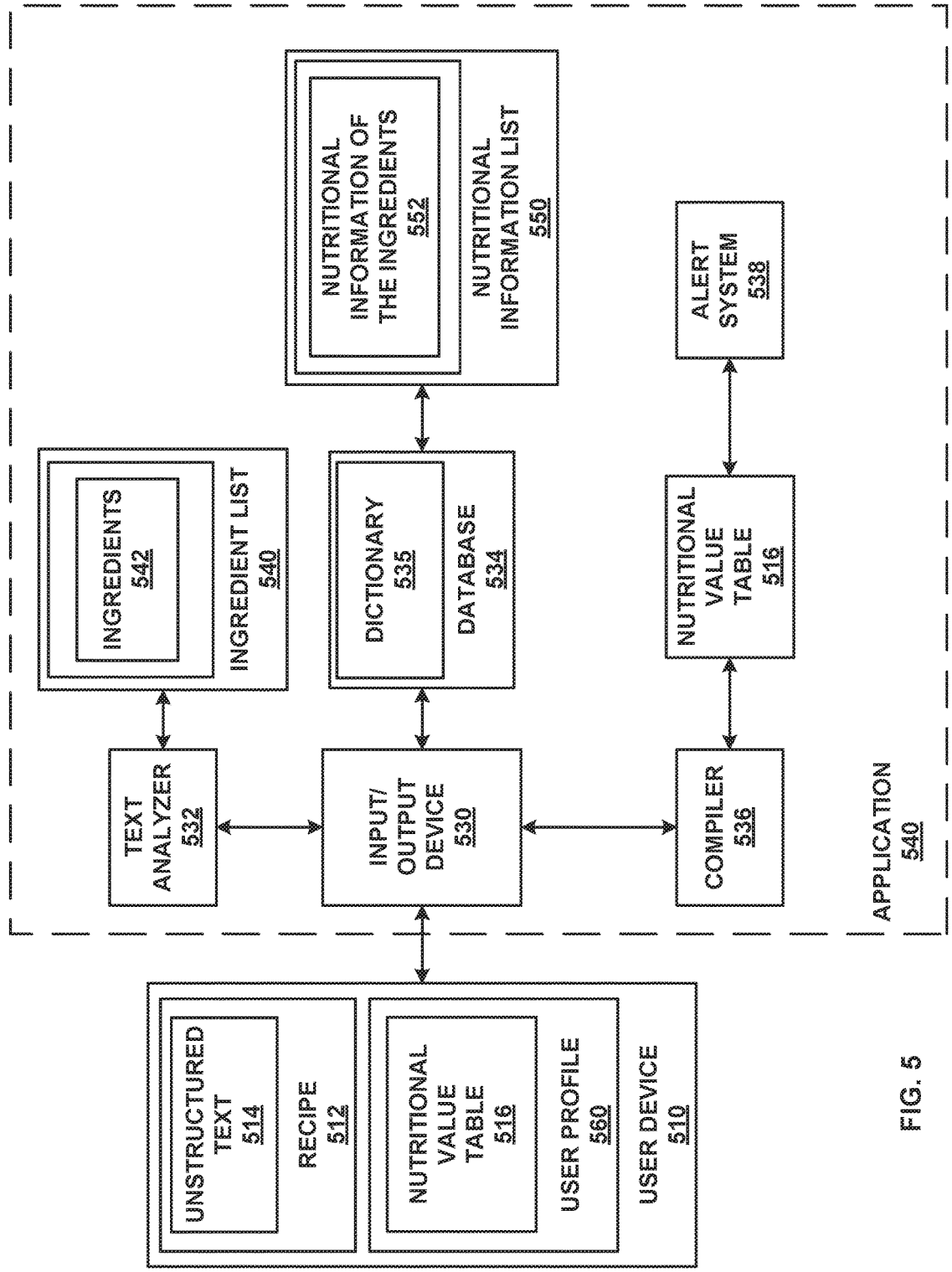
FIG. 5 depicts a diagram of an input/output device converting unstructured text of a recipe to a nutritional value table, according to embodiments of the present disclosure.

FIG. 5 depicts an input/output device receiving a recipe from a user device and outputting a nutritional value table for the recipe according to embodiments. An input/output device 530 is accessed by a user device 510 to convert a recipe 512 comprising unstructured text 514, into a nutritional value table 516. The input/output device 530 may be in communication with or be an interconnect between a text analyzer 532, a database 534, and a compiler 536.

The text analyzer 532 may receive a recipe 512 with unstructured text 514 from a user device 510. The text analyzer 532 may use the unstructured text 514 of the recipe 512 and output an ingredient list 540. The ingredient list 540 may include a plurality of ingredients 542. The plurality of ingredients 542 of the ingredient list 540 may be extracted from the unstructured text 514 by using a text analytics program of the text analyzer 532. In embodiments, extracting the ingredient list 540 may include the text analyzer 532 using UIMA. The gathering of the ingredients may include the text analyzer 532 using NLP. For example, the text analyzer 532 may gather an ingredient 542 of sugar from the recipe 512 from the unstructured text 514. Sugar may then be added as an ingredient 542 of the ingredient list 540. The ingredient list 540 may include a plurality of ingredients 542 extracted by the text analyzer 532.

The text analyzer 532 may include a repository that stores rules based on the nutritional information of the food. Once the ingredient is found within the recipe then the nutritional information of the ingredient may be retrieved. The rules of the ingredients may include a type of the ingredient. For example, a type of the ingredient may include unsalted butter, which has a lower sodium content than salted butter.

The database 534 may receive the ingredient list 540 and use a dictionary 535 to transform the ingredient list 540 of the recipe 514 to nutritional information list 550. The database 534 stores the dictionary 535, which includes the nutritional information for ingredients. For example, the dictionary 535 may gather the nutritional information of the ingredients from the USDA, which contains an updated repository of the nutritional indicators for ingredients. In some embodiments, the database 534 may receive the ingredient list 540 and may access the database 534 to search the dictionary 535 for the nutritional information of the ingredients 552. The nutritional information 550 may include the nutritional information off all of the ingredients within the ingredient list 540. Each ingredient within the ingredient list 540 may be correlated with an ingredient within the dictionary 535 of the database 534. The dictionary 535 may then output the ingredient as nutritional information. For example, if the ingredients 542 include a first ingredient that is sugar, then the dictionary 535 may look up the nutritional information of sugar. The nutritional information of sugar may then be outputted into the nutritional information list 550 as a nutritional indicator of an ingredient 552.

In various embodiments, the database 534 may also store ingredient information of substitutable ingredients as a substitution dictionary. The substitution dictionary may store a list of ingredients that correspond with one or more substitutable ingredients. The substitutable ingredients may be based on their nutritional indicator content, on a basis of similar taste, or a reduced nutritional indicator option. For example, a reduced nutritional indicator option could include a substitution for butter including unsalted butter. Unsalted butter could include a reduced nutritional indicator of sodium for butter. In an additional example, a basis of similar taste may include spinach, and iceberg lettuce. Spinach may be substituted for iceberg lettuce if the dietary preference of the user requires an increased iron intake. In an additional example, a nutritional indicator content substitution may include substituting an artificial sweetener for sugar. If the dietary preference of the user requires a reduced sucrose intake, an artificial sweetener may be substituted for sugar.

The compiler 536 may receive the nutritional information list 550 and combine the nutritional information of the ingredients 552 of the recipe 512 into a nutritional value table 516. The nutritional value table 516 of the recipe 512 may then be outputted by the input/output device 530 to the user device 510. The compiler 536 may combine each of the ingredients from the recipe 512 into a single nutritional value table 516 that a user may access from the user device 510. For example, the nutritional value table 516 may contain the combined nutritional information from each of the ingredients on the nutritional information list 550. The nutritional value table 516 may contain a combined nutritional information of the nutritional information of the ingredient 552. The nutritional value table 516 may then be outputted from the input/output device 530, and displayed on the user device 510 of the user.

The alert system 538 may determine that the nutritional value table 516 is not within dietary preferences of the user profile 560. The user profile 560 may include the dietary preference, which the user may set. An example of the dietary preferences may include a low sugar diet. If the nutritional value table 516 has a high sugar content, then the alert system may inform the user of the high sugar content.

The alert system 538 may inform the user that an ingredient does not correspond with a dietary preference of the user. The non-corresponding ingredient (offending ingredient or particular ingredient) may be displayed to the user or removed from the recipe to conform to the dietary preferences of the user.

The determination of a non-corresponding ingredient may cause the recipe to become a non-corresponding food recipe. The non-corresponding food recipe may include at least one ingredient of a plurality of ingredients that do not correspond with the dietary preferences of a user. For example, if an ingredient of chicken is determined to be a non-corresponding ingredient, then the non-corresponding ingredient will cause the food recipe to become a non-corresponding food recipe.

In various embodiments, the nutritional information of each ingredient may be outputted by the dictionary 535. The user of the user device 510 may request nutritional information of an ingredient from the nutritional information 550. The user may access the nutritional information for each ingredient comprising the recipe. For example, a user may request the nutritional information of ingredient A 542. If the user requests the nutritional information, they may access the ingredient list 540. The ingredient list may allow the user to see the nutritional information of each of the ingredients 552. The nutritional information of the ingredients 552 may include the nutritional information gathered from the database 534. The user may look at the ingredients of the recipe 512 independently and make decisions on the meal based on the ingredients 542 and the nutritional information of the ingredients 552.

In various embodiments, the alert system 538 may inform the user that the recipe 512 does not correspond with the dietary preferences by informing the user that the ingredient or nutritional indicator that causes the recipe 512 to not correspond with the dietary preferences. For example, a user may have a low sugar diet. If the recipe 512 includes adding sugar, then the sugar may be highlighted in an ingredient list 540 or on the nutritional value table 516.

In various embodiments, informing the user may include alterations to the recipe. The alterations may include visually differentiating the non-corresponding ingredients such as highlighting sugar on the nutritional value table, for a user with a low sugar diet. For example, the device may display a nutritional value table but the user is on a low sodium diet. The nutritional information of the ingredients 522 may determine that an ingredient 542 is high in sodium. The nutritional value table 516 may include highlighting the sodium content of the recipe 512.

In various embodiments, the nutritional value table 516 may be altered by the user or by the dietary preferences of the user by removing or adding an ingredient. Additions, removal, and substitutions of ingredients may cause the nutritional value table 516 to change. The user may change the recipe 512 in response to the altering of the nutritional information of the ingredients 552 in the recipe 512. If the user changes the ingredients 542 of the recipe 512, then the nutritional value table 516 may be updated.

An addition of an ingredient to the recipe may increase the nutritional indicators of the nutritional value table 516 of the recipe 512. An example of an addition may include adding cheese to a sandwich that originally did not have cheese. The type of cheese, the weight/volume of the cheese, and the unit of measurement may be added to the recipe. After the cheese is added to the recipe 512, the nutritional value table 516 may be updated. For example, if the cheese is added to the ingredient list 540 of the recipe 512, then the total calories of the recipe may increase.

A removal of an ingredient from the recipe 512 may decrease the nutritional indicators of the nutritional value table 516 of the recipe 512. An example of a removal may include removing cheese from a sandwich that originally had cheese. The type of cheese, the weight/volume of the cheese, and the unit of measurement may be removed from the recipe 512. After the cheese is removed from the recipe 512, the nutritional value table 516 may be updated. For example, if cheese is removed from the ingredient list 540 of the recipe 512, then the total calories of the recipe may decrease.

A substitution of an ingredient to the recipe may increase and/or decrease various nutritional indicators of the nutritional value table 516 of the recipe 512 depending on the substitution. An example of a substitution may include removing cheese and adding a different cheese from a sandwich. The type of the previous cheese, the weight/volume of the previous cheese, and the unit of measurement of the previous cheese may be removed from the recipe 512. The substitution of the new cheese, the weight/volume of the new cheese, and the unit of measurement of the new cheese may be added to the recipe 512. After the cheese is substituted from the recipe 512, the nutritional value table 516 may be updated. For example, if a first cheese is substituted for another cheese of the ingredient list 540 of the recipe 512, then the total calories of the recipe may increase or decrease depending on the substitution.

Figure 6:
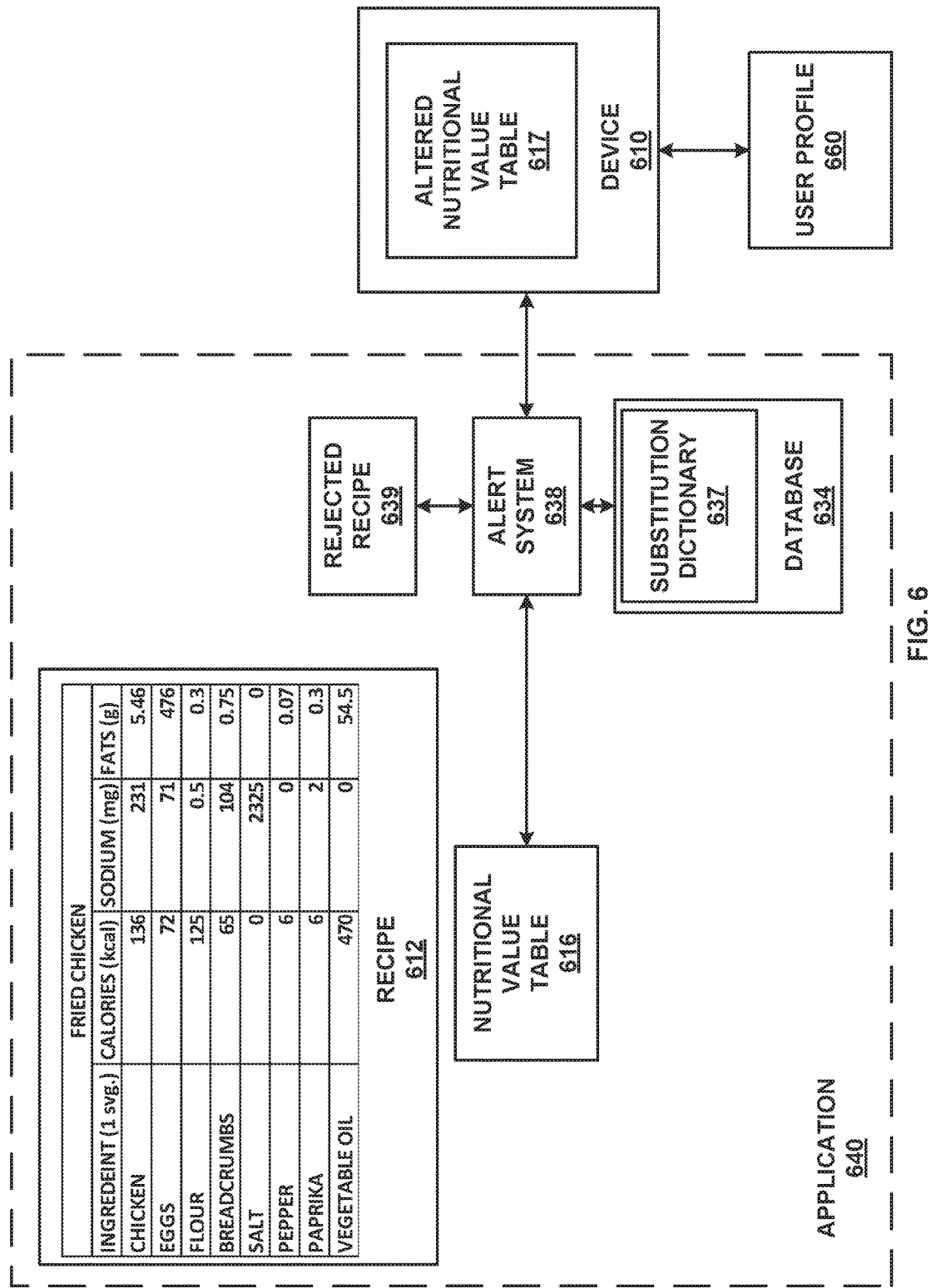
FIG. 6 depicts a nutritional value table being altered by substituting an ingredient of a recipe, according to embodiments of the present disclosure.

In FIG. 6, a nutritional value table is altered by substituting an ingredient from the substitution dictionary, or rejecting a recipe, according to embodiments. The nutritional value table 616 of a recipe 612 is compiled and the alert system 638 may determine that the recipe 612 is does not correspond with the dietary preferences of the user profile 660. The recipe 612 may include the ingredients and the amounts of the ingredients. For example, the recipe 612 includes the ingredients for a fried chicken recipe. The ingredients may also include nutritional indicators such as, calories in kilocalories (kcal), sodium in milligrams (mg), and fats in grams (g). If the alert system 638 determines that the nutritional indicators of the nutritional value table 616 do not correspond with the dietary preferences of the user 660, then the nutritional value table 616 may be altered or rejected. After altering, an altered nutritional value table 617 may be displayed on the device 610 to the user. The altered nutritional value table 617 may include an altered food recipe. The altered food recipe may include the ingredients of the original food recipe and the altered ingredients. The altered ingredients may include a removed, added, or substituted ingredient of the food recipe. The altered food recipe may be displayed to the user along with the altered nutritional value table 617.

The alert system 638 may communicate with a database 634, which includes a substitution dictionary 637. The substitution dictionary 637 may include a list of ingredients that are comparable substitutions for possible non-corresponding ingredients. The substitution dictionary may be stored within the database within the application or may be accessed through a network connection to an off device storage. A non-corresponding ingredient may include an ingredient that does not follow dietary preferences of a user from the user profile 660. The non-corresponding ingredient may cause the recipe to become a non-corresponding food recipe. A non-corresponding food recipe may include one or more non-corresponding ingredients that do not correspond with the dietary preferences of the user. For example, a non-corresponding ingredient may be vegetable oil for a dietary preferences requiring foods low in saturated fat. A list of comparable substitutions for vegetable oil may include but is not limited to olive oil, or canola oil. For example, olive oil may be substituted for vegetable oil if the dietary preferences of the user require a reduced saturated fat intake. In an additional example, applesauce may be substituted for vegetable oil if the dietary preferences of the user requires a reduced fats intake. If the vegetable oil is substituted from recipe 612, then the nutritional value table 616 may be altered by the alert system 638 and the substation dictionary 637 to become the altered nutritional value table 617.

The alert system 638 may be used to analyze the recipe against the dietary preferences of the user profile 660. The alert system 638 may be used in conjunction with the databased 634, which contains the substation dictionary 637. The alert system 638 may determine that the nutritional value table 616 of a recipe 612 does not follow the dietary preferences of the user profile 660. If the nutritional value table 616 or the recipe 612 does not follow the dietary preferences of the user profile 660, then the alert system may remove an ingredient, substitute an ingredient, or reject the recipe 639. If an ingredient of the recipe 612 does not follow the dietary preferences of the user profile 660, then the alert system 638 may remove the ingredient from the nutritional value table creating the altered nutritional value table. For example, if salt of the recipe 612 does not follow the dietary preferences of the user profile 660, then the alert system 638 may remove the salt from the nutritional value table 616 to create the altered nutritional value table 617. If an ingredient that was removed from the recipe 612 may be substituted for, then the alert system 638 may use the substitution dictionary 637 to substitute the removed ingredient creating the altered nutritional value table 637. For example, if vegetable oil does not follow the dietary preferences of the user profile 660, then the alert system 638 may remove vegetable oil from the recipe 612. The database 634 may then offer a substitution of olive oil that the alert system 638 may use to create an altered nutritional value table 617. If an ingredient of a recipe 612 does not follow the dietary preferences of the user profile 660, then the alert system may reject the recipe 612 as a rejected recipe 639. For example, if chicken of the recipe does not follow the dietary preferences, then the removal of chicken from the recipe may cause the alert system 638 to reject the recipe as a rejected recipe 639.

In various embodiments, a substation may include adding an additional ingredient to the recipe. If the dietary preferences of the user include heart health problems, then foods high in omega 3s may be added to the food recipe. If the user requires an intake of omega 3s with the meal, then the substitution dictionary may suggest ingredients that include omega 3s to be added to the recipe For example, a food recipe may allow for a substitution of adding salmon to the recipe. The addition of the salmon may fulfil the omega 3s requirement of the dietary preferences of the user.

The recipe 612 may be rejected if an ingredient of the recipe 612 does not correspond with the dietary preferences of the user, and makes up over a certain percentage of the recipe. If an ingredient is a large portion by weight or volume of the recipe and the ingredient is a non-corresponding ingredient, then the recipe may be rejected. For example, the recipe 612 includes chicken. If the user is a vegetarian, then the chicken may be a non-corresponding ingredient of the dietary preferences of the user profile 660. The recipe 612 may be rejected as a rejected recipe 639, on the determination that the chicken makes up over 50% of the recipe by weight.

In various embodiments, ingredients of a recipe 612 may be reduced to make recipe be with the dietary preferences of the user. If an ingredient may be reduced to make the recipe be within the dietary preferences, then the amount of the ingredient may be reduced. For example, the recipe 612 includes a sodium content of 2733.5 mg, the amount of salt may be reduced to lower the overall sodium content. If the salt is reduced in half, then the sodium content will be 1571 mg. If 15371 mg of sodium is within the dietary preferences of the user profile 660 for a meal, then the recipe 612 may be altered and the altered nutritional value table 617 may be displayed to the user on the device 610.

Figure 7:
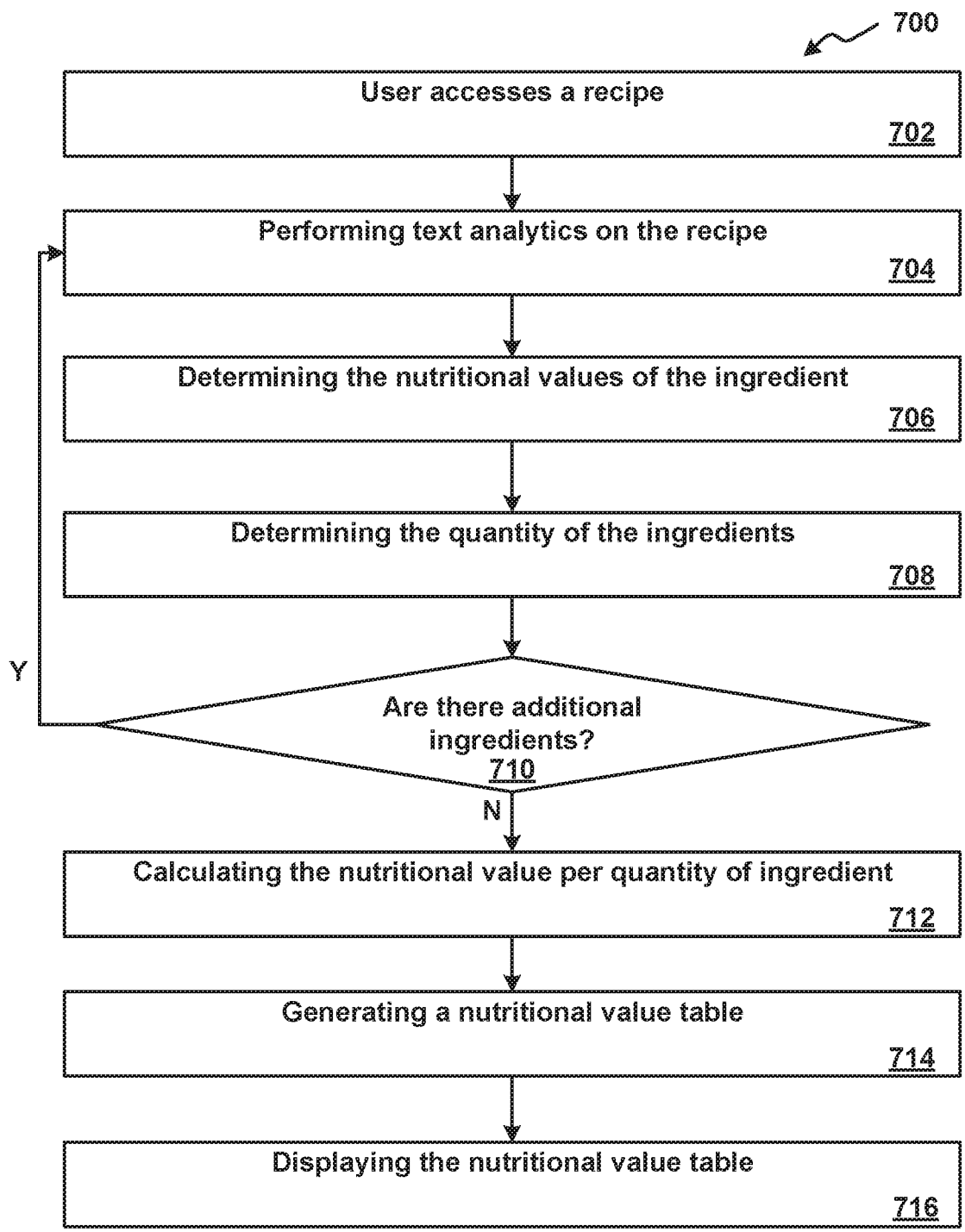
FIG. 7 depicts a flowchart of converting a recipe to nutritional value table, according to embodiments of the present disclosure.

In FIG. 7, a flowchart of a method 700 for converting a recipe to a nutritional value table is illustrated, according to embodiments. The method 700 generates and displays a nutritional value table based on a food recipe (recipe) to a user. The recipe may include a plurality of ingredients where each ingredient contains one or more nutritional indicators of the ingredient. The amount of nutritional indicators may be determined based on the amount of each of the ingredients within the recipe. The determined amount of nutritional indicators may then be compiled into the nutritional value table. The nutritional value table of the recipe may then be displayed to the user.

In operation 702, a user accesses a recipe to be converted to a nutritional value table. The recipe may include a list of ingredients and steps for preparing a specific meal. The recipe may consist of a plurality of ingredients each with nutritional value. A nutritional value may include nutritional indicators of each of the ingredients.

In operation 704, a text analyzer performs text analytics on the recipe to extract the plurality of ingredients. The recipe may be web based or locally stored on the device. The text analytics may include unstructured information management architecture (UIMA) or natural language processing (NLP) depending on the type of recipe. For example, the recipe may include five ingredients. A text analyzer may extract the unstructured text of the recipe though UIMA to determine the five ingredients within the recipe. UIMA may search the recipe to find the five ingredients that are listed in the recipe. UIMA may search HTML of the recipe; the UIMA may determine the ingredients based on the HTML. The ingredients may also include quantities and a unit of measurement of the quantity.

In various embodiments, the unstructured text may be located within the HTML, which includes reference numbers as ingredients. The text analyzer may access the reference numbers and a reference list of the recipe. The website may include an accessible reference list of the reference numbers the text analyzer may access to determine the ingredients of the recipe. For example, a recipe host may be a website, and the HTML of the recipe may include reference number for the ingredients. Alone, the reference number may not indicate the ingredient, but the reference number may be cross-referenced with the reference list of the website. After cross-referencing the reference number, the ingredient may be determined.

In operation 706, the text analyzer determines a plurality of ingredients that are included within the recipe. The plurality of ingredients may then be compared to an ingredient and nutrition database. The dictionary may include nutritional indicators of the plurality of ingredients. For example, the plurality of ingredients may include unsalted butter. Unsalted butter may be looked up within the ingredient and nutrition database to find the nutritional information.

The ingredient and nutrition database may include a dictionary that contains a list of ingredients and nutritional information of the ingredients. The dictionary may include nutritional information of the plurality of ingredients, which may be used to create a nutritional value table. The nutritional information may comprise the nutritional indicators of the plurality of ingredients. For example, an ingredient may be a stick of unsalted butter. The unsalted butter may include nutritional information of the unsalted butter based on the typical nutritional indicators of unsalted butter.

In operation 708, the text analyzer determines the quantities of each of the plurality of ingredients within the recipe. The amount of an ingredient may include the quantity of the ingredient, and a unit of measurement of the ingredient within the recipe. The amounts of the plurality of ingredients may then be compared to the ingredient and nutrition database. For example, the ingredient may be sugar. The amount of the sugar may include 1 cup, where 1 would be the quantity, and a cup may be a unit of measurement. The 1 cup measurement may be compared to the ingredient and nutrition database to determine the nutritional value of 1 cup of sugar.

In operation 710, the text analyzer determines whether or not additional ingredients are within the recipe or if ingredients have been added to the recipe. A user may want to update the recipe by adding or removing an ingredient from the recipe before the nutritional value table is compiled. If more ingredients are added, or a change is made to the recipe the method 700 may return to operation 704 where the recipe is determined with text analytics. For example, a user may substitute chicken for steak in a recipe. The nutritional value of the substitution may be inputted into the recipe and the nutritional value of the ingredients may be determined.

In operation 712, a dictionary provides the nutritional values per quantity for each of the plurality of ingredients of the recipe. The ingredient and nutrition database may be used to calculate the nutritional information of the plurality of ingredients. The nutritional information of each of the ingredients may be calculated based on how much of the ingredient is within the recipe. The nutritional information may include the nutritional indicators of the ingredients. The nutritional information of each of the ingredients may be combined into a nutritional value of the recipe. The nutritional value may include all of the ingredients determined from the recipe. For example, the recipe may include five ingredients. The nutritional information for each of the five ingredients may be combined into a nutritional value of the recipe.

In various embodiments, the serving size may be extracted from the recipe. NLP or UIMA may gather annotations or data from the unstructured text to gather the serving size information of the recipe. The gathered serving size information may then be used to determine the nutritional value table for one serving size. For example, the recipe may include a serving size. If the recipe calls for two steaks and the serving size of the recipe may be two serving sizes, then the nutritional information for two steaks may be divided by two for each serving to be one steak.

In operation 714, a compiler compiles the nutritional values for each of the plurality of ingredients into a nutritional value table. Each of the nutritional values of the plurality of ingredients may be compiled into a nutritional value table. The nutritional value table may contain a summation of each of the nutritional indicators making up the nutritional information of each of the plurality of ingredients. For example, if the recipe consists of five ingredients, then the nutritional information of all five ingredients may be combined to make a nutritional value table.

In operation 716, an input/output device displays the nutritional value table to the user. The displayed nutritional value table may be accessed by a user to determine the nutritional value of the recipe. The nutritional value table may be displayed on a device the user may access. For example, the nutritional value table may be displayed on a GUI.

Figure 8:
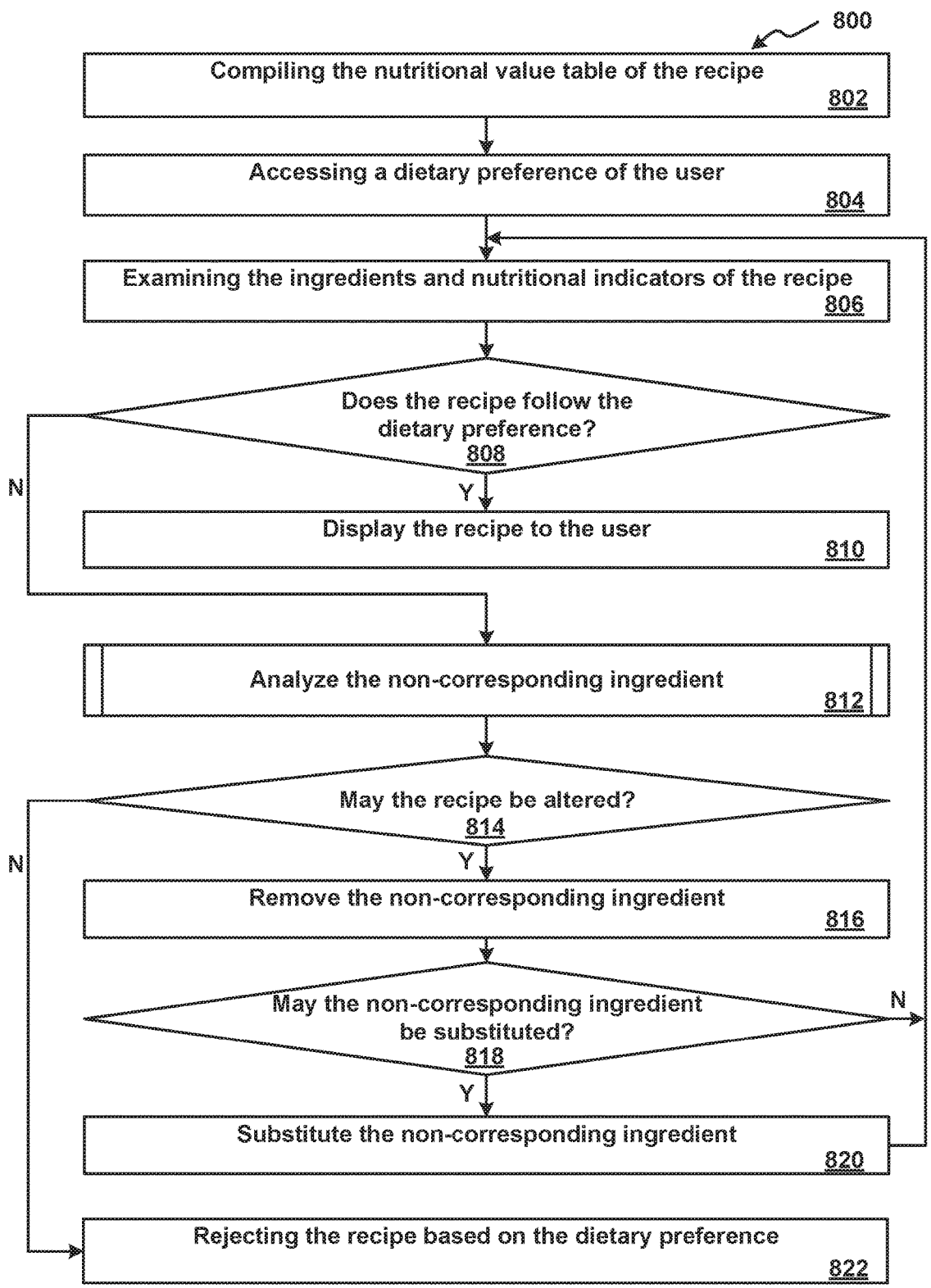
FIG. 8 depicts a flowchart of a recipe being altered based on dietary preferences of a user, according to embodiments of the present disclosure.

In FIG. 8 a flowchart of a method 800 of a recipe being altered based on dietary preferences of a user is illustrated, according to embodiments. The method 800 may include an alert system that may determine if a recipe follows a dietary preference(s) of the user. A dietary preference may include eating preferences that may restrict or cause the user to consume or not consume certain ingredients or constituents of a food recipe. The recipe may be analyzed by an application, which compiles a nutritional value table and determines the dietary preferences of a user profile.

In operation 802, a compiler compiles a nutritional value table from the recipe. A nutritional value table may include the nutritional information of a food recipe. The food recipe may contain the nutritional indicators of each of the ingredients compiled into one nutritional value table. For example, a recipe may consist of five ingredients. The nutritional information of each of the five ingredients are compiled into a single nutritional value table.

In operation 804, an alert system accesses the dietary preferences of the user. The dietary preferences of the user may be contained in a user profile. The user profile may contain at least one dietary preferences that may be accessed. The dietary preferences may include diets the user may follow based on their daily consumption of food. For example, the user may have a low sodium diet. The low sodium diet may be a dietary preference, which the recipe may be checked against to determine if the recipe follows the diet of the user.

In operation 806, the alert system examines the ingredients of the recipe. The ingredients are examined and the nutritional indicators of the ingredients may be calculated. The ingredients and nutritional indicators may include the quantities of the ingredients. For example, the recipe may be gathered by text analytics. The ingredients may then be determined if the ingredients and the nutritional indicators follow the dietary preferences of the user in operation 808.

In operation 808, an alert system determines whether or not the recipe follows the dietary preferences of a user profile. If the recipe is within the dietary preferences of the user, then the recipe may be approved and the method 800 may progress to operation 808. For example, the dietary preferences of the user may include a low calorie diet. If the recipe in low in calories with respect to a total caloric intake, then operation 806 may determine that the recipe follows the dietary preferences of the user. If the recipe follows the dietary preferences of the user profile, then the method 800 may progress to operation 810. If the recipe does not follow the dietary preferences of the user, then the recipe may require alteration. If the recipe requires alteration, the method 800 may progress to operation 812. For example, the dietary preferences of the user may include a low calorie diet. If the recipe is not low in calories with respect to a total caloric intake of the dietary preferences of the user, then the recipe may be determined to not correspond with the dietary preferences of the user.

In various embodiments, the dietary preferences within a user profile may be accessed and determined by an input/output device of an application. The application may contain the input/output device, which is communicatively coupled with a text analyzer, a database, and a compiler. The application may use the input/output device to analyze the recipe to determine if the recipe follows the user profile.

In various embodiments, the recipe may be determined if the recipe follows the dietary preferences based on an intake of the user intakes over a period of time. The intake of the user over a period of time may include the foods the user consumed throughout the day. The intake of the user over a period of time may include the foods the user consumed within a numbered hour period. For example, the dietary preferences of the user may restrict the user to consume only a predetermined amount of calories user over a period of time. If the calories of the recipe are less than the predetermined amount, then the recipe may be displayed to the user in operation 810.

In operation 810, an input/output device displays the recipe to the user. If the recipe follows the dietary preferences of the user, then the recipe may be displayed to the user. For example, the user profile may include dietary preferences of a low sodium diet. If the sodium of the recipe is below the dietary preferences of the user, then the recipe may be approved and displayed to the user.

In various embodiments, the recipe may be approved if the recipe follows the dietary preferences by a percentage of a daily intake. The percentage of the daily intake may be determined by a nutritional indicator the user may consume within the day and split the daily intake by the number of meals the user eats a day. For example, if the user eats three meals a day, the percentage of daily intake may be 33.3%. If the recipe is under 33.3% of a nutritional indicator of the dietary preference, then the recipe may be displayed to the user. For example, if the dietary preferences of the user include a low sodium diet, then the nutritional indicator may be sodium. If the sodium content is less than 33.3% of the daily intake, then the recipe may be displayed to the user.

In operation 812, the alert system analyzes the non-corresponding ingredient that does not correspond with the dietary preferences of the user (i.e. an offending ingredient, or a particular ingredient). The recipe may be altered based on the determination of the non-corresponding ingredient. The alteration may include identifying a nutritional indicator that the non-corresponding ingredient causes the recipe to not correspond with the dietary preferences of the user. For example, the user may have a low sodium diet. If the recipe includes adding a pinch of salt, then the pinch of salt may be shown as an alteration on the nutritional value table. The pinch of salt may have a nutritional indicator of sodium that conflicts with the dietary preferences of the user. If the recipe may be altered, then the method 800 may progress to operation 812 where the alteration is displayed to the user. If the recipe may not be altered, then the method 800 may progress to operation 814 where the recipe is rejected.

In various embodiments, the analyzation of the recipe may include searching a database of related ingredients. The related ingredients database may be used for a substitution. In some embodiments, the related ingredient may be a list of substitutable ingredients based on dietary preferences. For example, related ingredients may include butter and unsalted butter. If the recipe calls for butter, but the dietary preferences of the user include a low sodium diet, the unsalted butter may be substituted for the butter. The substitution may reduce the sodium of the recipe, which may be displayed as an alteration to the user.

In various embodiments, the alteration may include removing an ingredient from the recipe. The dietary preferences of the user may include altering the nutritional value table based on a removal of an ingredient. For example, the dietary preferences of the user may include vegetarianism. If the user is vegetarian and the recipe contains chicken, then the chicken may be removed as an alteration to the nutritional value table.

In operation 814, the alert system may determine if the particular ingredient may be removed, altering the recipe. The recipe may include a particular ingredient that does not correspond with the dietary preferences of the user. The non-corresponding ingredient may be removed from the recipe. To determine if the recipe may be altered the non-corresponding ingredient may be compared to the rest of the recipe to determine an ingredient makeup of the recipe. The ingredient makeup of the recipe may be used to determine how much of the non-corresponding ingredient makes up the recipe and the amount may be a threshold. If the recipe may not be altered, then the method 800 may progress to operation 822 where the recipe is rejected. For example, if the recipe does not follow the dietary preferences of the user and the recipe includes an ingredient that may not be removed, then the recipe may be rejected in operation 822. If the recipe may be altered, then the method 800 may progress to operation 816 where the non-corresponding ingredient is removed from the recipe. For example, if the non-corresponding ingredient includes a pinch of salt and the pinch of salt may be removed, then the method 800 may progress to operation 816.

In various embodiments, the threshold for a non-corresponding ingredient may be half of the recipe by weight. The recipe may be rejected based on the weight or amount of the non-corresponding ingredient. If the non-corresponding ingredient makes up more than half of the recipe in weight, then the method 800 may progress to operation 822 and the recipe may be rejected. For example, the dietary preference of the user is vegetarianism, the non-corresponding ingredient is chicken, and the recipe is for fried chicken. If the fired chicken recipe is more than half by weight chicken, then the fried chicken recipe may be rejected and the method may progress to operation 822. In an additional example, if the non-corresponding ingredient makes up less than half of the recipe in weight, then the method 800 may progress to operation 816 where the non-corresponding ingredient is removed. For example, the dietary preference of the user is low sodium, the non-corresponding ingredient is a pinch of salt, and the recipe is for grilled chicken. If the fired chicken recipe is less than half by weight a pinch of salt, then the recipe may be altered.

In various embodiments, the non-corresponding ingredient may be determined by the ingredient. The ingredient that has been determined to be a non-corresponding ingredient may include a type or family of ingredient that does not follow the dietary preferences of the user. For example, the user has a dietary preference of a peanut allergy. If the recipe contains peanuts and the peanuts are not removable, then the recipe may be rejected.

In operation 816, the alert system may remove the non-corresponding ingredient. Removing the non-corresponding ingredient may include altering the recipe. Altering the recipe may include altering the nutritional value table. If the non-corresponding ingredient may be removed from the recipe, then the ingredient may be removed and the nutritional information may be updated. For example, the user may have dietary preferences of low sodium and the non-corresponding ingredient is a pinch of salt. The pinch of salt may be removed from the recipe and the dietary preferences may be updated.

In operation 818, a substitution dictionary may determine if an ingredient may be substituted for the removed non-corresponding ingredient. The non-corresponding ingredient that was removed in 816 may be substituted for an ingredient that may be found in a substitution dictionary within a database. The substitution may include determining the non-corresponding ingredient, and determining an ingredient that may be substituted for the non-corresponding ingredient in operation 820. For example, a non-corresponding ingredient of butter may be determined, with a user with dietary preferences of a low sodium diet. The database including the substitution dictionary may determine that unsalted butter is a substitution for butter for the recipe. If the substitution of unsalted butter is a substitution for the butter of the recipe, then the substitution may be performed. If the substitution dictionary determines that there is not a substitution for the non-corresponding ingredient, then the method 800 may return to operation 806 where the ingredient and nutritional indicators are examined. For example, a non-corresponding ingredient may be steak of a grilled steak recipe, and the user has dietary preferences of vegetarianism. If the substitution dictionary determines that the steak may not be substituted, then the steak will be removed from the recipe and a substitution may not be performed.

In operation 820, the substitution dictionary may substitute the non-corresponding ingredient. If a recipe includes an ingredient that does not correspond with the dietary preferences of a user, the ingredient may be substituted for a comparable ingredient. The comparable ingredient may be determined by a substitution dictionary, which determines which ingredients may be substituted for another. For example, the non-corresponding ingredient that was removed is chicken, and the dietary preference is vegetarianism. If a non-animal meat product like tofu is determined substitutable by the substitution dictionary, then tofu may be substituted in the recipe. After substitution, the method may progress to operation 806, where the ingredients and nutritional indicators of the recipe are examined.

In various embodiments, the user may input a substitution. The user may select the non-corresponding ingredient that does not correspond with the dietary preferences of the user, and select or input a substitution. For example, a user may substitute chicken in place of steak of a recipe. The ingredients and nutritional indicators may be examined in operation 806.

In operation 822, the alert system may reject the recipe based on the recipe being unable to be altered and the user profile. The recipe may be rejected if the recipe may not be altered. If a removal or a substitution of an ingredient is not possible, then the recipe may be rejected. For example, the recipe includes grilling a steak, and the dietary preference includes vegetarianism. The application may inform the user that the recipe is not within the dietary preferences of the user and reject the recipe.

In various embodiments, the rejection of the recipe may be determined based on the ingredient makeup of the recipe. The ingredient makeup may include a percentage by weigh/volume of the ingredient compared to the rest of the recipe. If the ingredient makeup of a non-corresponding ingredient is more than a determined percentage, then the recipe may be rejected. For example, the dietary preferences of the user may be vegetarianism. The determined percentage may be calculated based on daily values of the consumption of the user. If the non-corresponding ingredient chicken makes up more than the determined percentage, the recipe may be rejected.

Figure 9:
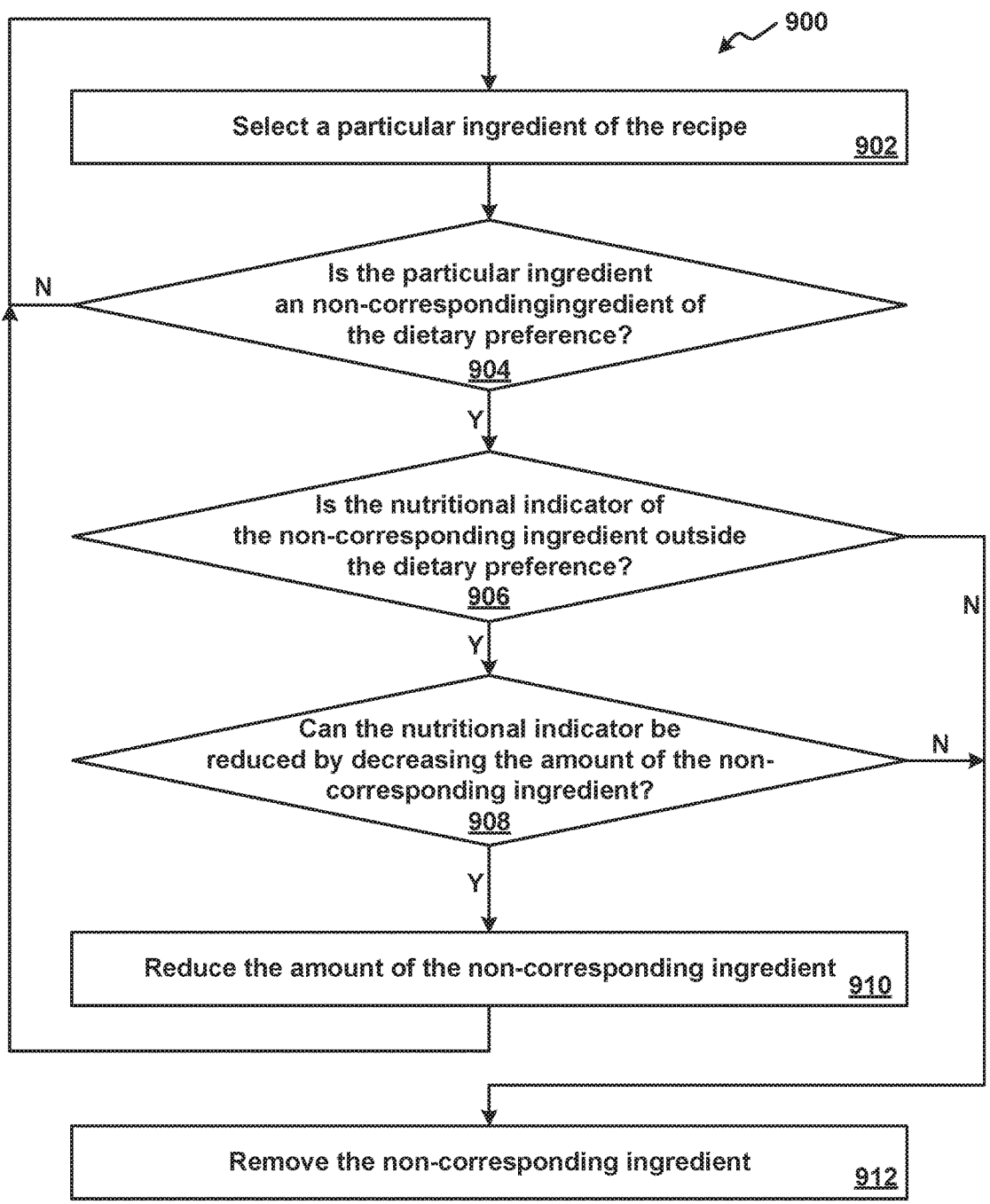
FIG. 9 depicts a flowchart where a particular ingredient is determined, according to embodiments of the present disclosure.

In FIG. 9, a flowchart of method 900 where a particular ingredient is determined, according to embodiments. The method 900 may correspond to operation 812 of FIG. 8. The recipe is determined if a particular ingredient is a non-corresponding ingredient that may be removed, or that may be reduced to no longer be a non-corresponding ingredient.

In operation 902, an alert system may select an ingredient of the recipe. The recipe may be analyzed to determine the ingredients of the recipe. One of the ingredients of the recipe is selected from a list compiled by analyzing the recipe. For example, if a list of the ingredients of a recipe for grilled steak includes steak, the steak may be selected as an ingredient.

In operation 904, the alert system determines if the particular ingredient that was selected is a non-corresponding ingredient of the dietary preferences of a user. If the particular ingredient is the non-corresponding ingredient, then the method 900 may progress to operation 906. For example, the dietary preferences of the user may be a low sodium diet, and the non-corresponding ingredient may be butter. The butter may be selected as a non-corresponding ingredient if it contains enough sodium. If the particular ingredient is a corresponding ingredient, then the method 900 may return to operation 902 and select another particular ingredient. For example, if the dietary preference of the user is a low sugar diet and the particular ingredient is a zero sugar yogurt. The zero sugar yogurt may not be the non-corresponding ingredient because the zero sugar yogurt may contain zero grams of sugar.

In operation 906, the alert system determines if a nutritional indicator of the non-corresponding ingredient does not correspond with the dietary preferences of the user. If the dietary preference of the user is determined by nutritional indicators, the recipe may be altered based on the nutritional information of the ingredient not the ingredient itself. For example, if the dietary preference of the user is vegetarianism, then the non-corresponding ingredient may not be based on the nutritional indicators of a recipe including chicken. If the recipe is not based on the nutritional indicators of the recipe, then the method 900 may progress to operation 912 where the recipe is altered. In another example, if the dietary preference of the user is a low sodium diet, then the non-corresponding ingredient may be based on the nutritional indicators of a recipe including a pinch of salt. If the recipe is based on the nutritional indicators of the recipe, then the method 900 may progress to operation 908 where the amount of the non-corresponding ingredient may be reduced.

In operation 908, the alert system determines if the amount of the non-corresponding ingredient may be reduced. The amount of the non-corresponding ingredient may be reduced to allow the recipe to correspond the dietary preferences of the user. If the ingredient may be reduced by a predetermined amount correspond the dietary preferences the amount of the ingredient may be reduced. For example, if the non-corresponding ingredient is soy sauce and the dietary preferences is low sodium, then the amount of soy sauce may be reduced. If the amount of the ingredient may be reduced, then the method 900 may progress to operation 910. In another example, if the non-corresponding ingredient is pork and the dietary preference is low calories, then the ingredient may not be able to be reduced. If the ingredient may not be reduced, then the method may progress to operation 912.

In operation 910, the alert system reduces the amount of the non-corresponding ingredient. If the amount of the non-corresponding ingredient may be reduced, then the amount may be reduced and the method 900 may return to operation 902 where the particular ingredients of the recipe are selected. For example if the amount of soy sauce is reduced, then the amount of sodium may have been reduced enough to no longer is a non-corresponding ingredient in operation 904.

In operation 912, the alert system may remove non-corresponding ingredient from the recipe. If the amount of the ingredient cannot be reduced then the ingredient may be removed from recipe. For example, if a pinch of salt is a non-corresponding ingredient and cannot be reduced, then the pinch of salt may be removed from the recipe.

The present invention may be a system, a computer implemented method, and/or a computer program product. The computer program product may include a computer readable storage medium (or media) having computer readable program instructions thereon for causing a processor to carry out aspects of the present invention.

The computer readable storage medium may be a tangible device that may retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein may be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, may be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that may direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, may be implemented by special purpose hardware-based systems that perform the specified functions or acts or carry out combinations of special purpose hardware and computer instructions.

What is claimed is:

1. A computer-implemented method, executed by a computing device, for determining nutritional information of a food recipe using text analytics, comprising:
    analyzing, by a text analyzer configured to implement unstructured information management architecture and natural language processing, an unstructured text of a food recipe as instructions for preparing a meal to generate an ingredient list for the food recipe from the unstructured text to obtain:
        a plurality of ingredients for the food recipe,
        a quantity of each of the plurality of ingredients, and
        a number of servings;
    accessing a set of dietary preferences of a user from a user profile associated with the user;
    calculating nutritional information of each of the plurality of ingredients using the quantity of the plurality of ingredients within the food recipe;
    compiling, by a compiler, the nutritional information of the plurality of ingredients into a nutritional value table, by:
        accessing a database, wherein the database includes:
            a nutritional information dictionary, including a list of ingredients and a nutritional indicators per quantity of the ingredients, and
            a nutritional value, calculated from the ingredient and a nutrient value per quantity, of the nutritional indicators of the list of ingredients,
        gathering the nutritional value of each of the plurality of ingredients from the nutritional information dictionary, and
        calculating the nutritional information of each of the plurality of ingredients using the quantity of each of the plurality of ingredients;
    determining whether the food recipe corresponds with the set of dietary preferences of the user, by comparing the calculated nutritional information for the plurality of ingredients with the dietary preferences of the user contained in the user profile, wherein a non-corresponding food recipe includes a first ingredient from the plurality of ingredients that does not correspond with the set of dietary preferences of the user, the first ingredient including a nutritional indicator that does not correspond with the set of dietary preferences of the user;

alerting, via an alert system the user that the first ingredient does not correspond with the set of dietary preferences of the user;

displaying, on a display device, to the user the first ingredient that does not correspond with the set of dietary preferences of the user;

altering, by the alert system, in response to determining a non-corresponding food recipe, the food recipe by removing the first ingredient;

substituting, in response to removing the first ingredient from the non-corresponding food recipe, a second ingredient for the first ingredient, by the alert system in conjunction with the database, wherein the substituting the second ingredient includes:

accessing a substitution dictionary of substitutable ingredients for the first ingredient, determining whether the second ingredient is present in the substitution dictionary as a substitute for the first ingredient, updating the nutritional information dictionary of the database, adding the second ingredient a respective quantity to the plurality of ingredients of the food recipe, accessing the nutritional information of the second ingredient, and updating the nutritional value table of the food recipe with the substitution of the second ingredient; and displaying the altered food recipe as a second nutritional value table.

\* \* \* \* \*